(12) United States Patent
McGuinness

(10) Patent No.: US 6,485,508 B1
(45) Date of Patent: Nov. 26, 2002

(54) LOW PROFILE STENT

(76) Inventor: Colm P. McGuinness, 9 Tearmann Eala, Ballyloughaum Rd., Renmore Galway (IE)

( * ) Notice: Subject to any disclaimer, the term of this patent is extended or adjusted under 35 U.S.C. 154(b) by 17 days.

(21) Appl. No.: 09/687,455

(22) Filed: Oct. 13, 2000

(51) Int. Cl.[7] .................................................. A61F 2/06
(52) U.S. Cl. ..................................................... 623/1.15
(58) Field of Search ............................... 623/1.16, 1.17, 623/1.15

(56) References Cited

U.S. PATENT DOCUMENTS

| | | |
|---|---|---|
| 5,421,955 A | 6/1995 | Lau et al. |
| 5,449,373 A | 9/1995 | Pinchasik et al. |
| 5,643,312 A | 7/1997 | Fischell et al. |
| 5,776,161 A | 7/1998 | Globerman |
| 6,013,091 A * | 1/2000 | Ley et al. .................. 623/1.16 |
| 6,066,169 A | 5/2000 | McGuinness |
| 6,090,127 A | 7/2000 | Globerman |
| 6,113,627 A * | 9/2000 | Jang ........................... 623/1.49 |
| 6,179,867 B1 * | 1/2001 | Cox ............................ 623/1.15 |
| 6,261,319 B1 * | 7/2001 | Kveen et al. .............. 623/1.15 |
| 6,331,189 B1 * | 12/2001 | Wolinsky et al. .......... 623/1.15 |
| 6,334,871 B1 * | 1/2002 | Dor et al. ................... 623/1.34 |

FOREIGN PATENT DOCUMENTS

| | | |
|---|---|---|
| EP | 0 876 806 A1 | 11/1998 |
| WO | WO 97/33534 A1 | 9/1997 |
| WO | WO 00/62710 A1 | 10/2000 |

* cited by examiner

Primary Examiner—Paul B. Prebilic
Assistant Examiner—William H Matthews
(74) Attorney, Agent, or Firm—Catherine C. Maresh; James F. Crittenden

(57) ABSTRACT

A stent having a hollow, cylindrical body made with a plurality of rings. The rings each extend circumferentially around the cylindrical body and include an undulating series of angulated peaks and valleys. The rings are joined together by a series of links, the rings and links being shaped and arranged to promote a very low compressed profile and longitudinal flexibility during stent delivery on the catheter and effective scaffolding after deployment. The rings are provided with inflection points on some portions of the rings which extend in a generally circumferential direction for a short distance.

19 Claims, 2 Drawing Sheets

LOW PROFILE STENT

FIELD OF THE INVENTION

The invention relates to intraluminal endovascular stenting, and in particular, to a low profile stent.

BACKGROUND OF THE INVENTION

Endovascular stenting is particularly useful for arteries which are blocked or narrowed and is an alternative to surgical procedures that intend to bypass the occlusion. The procedure involves inserting a prosthesis into a body lumen and expanding it to prevent collapse of a vessel wall. While stenting has most commonly been used adjunctively, following an intervention such as angioplasty or atherectomy, there is increasing interest in primary, or direct stent placement.

Percutaneous transluminal angioplasty (PTCA) is used to open coronary arteries which have been occluded by a build-up of cholesterol fats or atherosclerotic plaque. Typically, a guide catheter is inserted into a major artery in the groin and is passed to the heart, providing a conduit to the ostia of the coronary arteries from outside the body. A balloon catheter and guidewire are advanced through the guiding catheter and steered through the coronary vasculature to the site of therapy. The balloon at the distal end of the catheter is inflated, causing the site of the stenosis to widen. The dilatation of the occlusion, however, can form flaps, fissures and dissections which threaten re-closure of the dilated vessel or even perforations in the vessel wall. Implantation of a stent can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

A stent is typically a cylindrically shaped device formed from wire(s) or a tube and is intended to act as a permanent prosthesis. A stent is deployed in a body lumen from a radially compressed configuration into a radially expanded configuration which allows it to contact and support a body lumen. The stent can be made to be radially self-expanding or expandable by the use of an expansion device. The self-expanding stent is made from a resilient springy material while the expandable stent is made from a material which is plastically deformable. A plastically deformable stent can be implanted during an angioplasty procedure by using a balloon catheter bearing a crimped, or compressed stent which has been loaded onto the balloon. The stent radially expands as the balloon is inflated, forcing the stent into contact with the body lumen, thereby forming a supporting relationship with the vessel wall. Deployment is effected after the stent has been introduced percutaneously, transported transluminally and positioned at a desired location by means of the balloon catheter.

A balloon of appropriate size and pressure is first used to open the lesion. The process can be repeated with a stent loaded onto a balloon. Direct stenting involves simultaneously performing angioplasty and stent implantation using a stent mounted on a dilatation balloon. The stent remains as a permanent scaffold after the balloon is withdrawn. A balloon capable of withstanding relatively high inflation pressures may be preferable for stent deployment because the stent must be forced against the artery's interior wall so that it will fully expand, thereby precluding the ends of the stent from hanging down into the channel, encouraging the formation of thrombus.

In adjunctive stenting, a stent delivery system with a small diameter profile is not required because the narrowing has already been enlarged by the preceding device. However, in direct stenting, the stent and delivery balloon catheter need to be inserted into a stenosis that has not been previously dilated. Thus, for direct stenting to be applicable to many patients, the stent and delivery system must have a very low profile. The primary advantage of direct stenting is the procedural efficiency gained by eliminating a primary angioplasty step. The resulting procedure can be shorter and less expensive.

Primary angioplasty followed by stent placement typically requires a catheter exchange, which is usually performed over a guidewire. Given the prevalence of this staged procedure, the most commonly used balloon catheters have been over-the-wire types, having either a full length guidewire lumen or a short, distal guidewire lumen as found in rapid exchange catheters. Fixed wire, or "balloon-on-a-wire" type balloon catheters have been seldom used for primary angioplasty in stenting procedures, and these catheters have not been used to deliver stents at all. With their small size and wire-like trackability, fixed wire catheters are able to provide relatively quick and simple balloon placement and access to lesions that cannot be reached with other types of catheters. The small size of fixed wire catheters also permits their use through very small guiding catheters. However, these balloon catheters lack the ability to maintain guidewire position across a lesion for exchange purposes and they may encounter problems re-crossing a dilated area. Another reason that fixed wire balloon catheters have not been used for stent delivery is that the very small deflated profile of the balloon on such a catheter may be too small to securely carry a compressed stent of conventional design.

Previous structures used as stents or intraluminal vascular grafts have included coiled stainless steel springs, helically wound spring coils made from a shape memory alloy, expanding metal stents formed in a zig-zag pattern, and diamond shaped, rectangular shaped, and other mesh and non-mesh designs. Exemplary stent devices are disclosed in U.S. Pat. No. 5,776,161 issued to Globerman, U.S. Pat. No. 5,449,373 issued to Pinchasik et al, U.S. Pat. No. 5,643,312 issued to Fischell et al and U.S. Pat. No. 5,421,955 issued to Lau et al.

Problems to be overcome in stent design include inadequate radial force to maintain stent expansion, inadequate scaffolding of tissue against the wall, predilatation longitudinal rigidity that negatively impacts on stent delivery, and shortening of the stent as a consequence of radial expansion. Predilatation longitudinal rigidity is a significant stent shortcoming that prevents the threading of the stent through long tortuous vessels and lesions. Shortening of the stent is also a problem, as it is important that the stent cover the entire lesion to minimize the risk of post-operative complications. Many of these problems result from the often conflicting goals of stent design. For example, to provide uniform support to the vessel wall, it is desirable to have a high degree of scaffolding in the stent when it is expanded to its nominal radial size. However, it is also desirable to have a small, relatively smooth delivered profile when the stent is mounted on the catheter to permit the stent and catheter to traverse small diameter lesions. The person skilled in the art will appreciate that, as a stent with a very small delivered profile expands radially, its structural elements become farther apart and create openings which reduce the amount of scaffolding available to support the vessel. A similar situation exists with respect to the conflicting goals of improved scaffolding and flexibility during catheter delivery since proper scaffolding will not be accomplished if there are too few supporting structural elements. However, a stent with too many structural elements may be difficult to crimp small enough to fit onto the balloon catheter such that the structural elements do not abut or interfere with each other during delivery through tortuous vessels. Also, in some stents, during plastic deformation of the stent (i.e. balloon expansion), the strain is concentrated at small zones. This limits the properties of the material that can be used as well as the radial force and the expansion rate.

Co-pending U.S. patent application Ser. No. 09/292,991, entitled Medical Device for Intraluminal Endovascular Stenting, addresses a number of these issues. The '991 application discloses an expandable stent having a small initial diameter, flexibility along its longitudinal axis prior to expansion and minimization of rigid local strain on the stent material by the presence of rotation joints which have minimal strain during stent expansion. The stent of the '991 application has substantially the same length before and after expansion and it is easy to deliver, being longitudinally flexible when constrained. However, the delivery of such a stent on very low profile, fixed wire delivery catheters requires additional improvements in the size of the minimal crimped diameter.

SUMMARY OF THE INVENTION

The stent of the present invention has a hollow, cylindrical body made with a plurality of rings. It is manufactured from tubing having a diameter between a minimal crimped diameter of the stent and a nominal size that is closely matched to the size of the vessel to be treated. In the manufactured form of the stent, each ring extends circumferentially around the cylindrical body and includes an undulating series of peaks and valleys. The undulating peaks and valleys of each ring are formed by opposing angled segments, which are joined to each other by substantially straight struts. Adjacent rings are joined together by a circumferentially disposed series of links, which are shaped and arranged to promote longitudinal flexibility as the stent is delivered by the catheter. The links also promote effective scaffolding after stent deployment and prevent shortening of the stent as it is expanded.

Each ring is provided with inflection points, which may be substantially centered on the struts that extend between adjacent peaks and valleys of the ring. At each inflection point, a portion of the ring extends in a generally circumferential direction for a short distance, producing an offset in the otherwise straight strut. A link is joined at one end to an inflection point on one ring and the link is also joined at a second end to a second inflection point on an adjacent ring. Preferably, when the stent device is unexpanded, each link includes at least two angled segments that are capable of deflecting to promote longitudinal flexing of the stent when it is subjected to bending forces, such as those encountered during delivery of the stent and catheter through a tortuous vascular anatomy. Also preferably, each inflection point has a length, measured circumferentially, which is at least as great as the width of the link to which it is attached. Preferably, the circumferential length of the inflection point is no more than about twice the width of the link to which it is attached. When the stent is crimped on the balloon catheter, the links can fit closely together in a nested arrangement with the undulations of the rings. When the stent is expanded, vessel scaffolding is promoted by this nested arrangement, which allows a large number of connecting links. The terms "nest", "nested" or nesting" are used herein to mean that the elements are conformally arranged such they can be in very close proximity when the stent is crimped and loaded onto a catheter but without substantial contact that would affect the ability of the various elements to move in relation to each other as the stent and catheter are advanced through a tortuous body vessel. In some embodiments of the invention, only one link is connected to an inflection point. This makes the inflection point a "dead end" and permits some of the flexing forces which are not absorbed by the link itself to be absorbed by the rings to which it is attached. The links are arranged to provide flexibility, and the peaks and valleys of the rings are paired with each other in an in-phase relationship. Preferably, the rings are joined by multiple links, most preferably three or more links, and each ring has the same number of inflection points as the number of attached links. When a large number of connecting links are employed, the angles in the links are preferably of a complimentary shape to each other such that they will nest together when the stent is crimped for mounting onto the catheter.

Another aspect of the invention is the conformal nesting of ring and link components such that the stent can be readily crimped for loading onto a balloon or other expansion device on the catheter. A stent made according to the present invention may be made from a tube which is cut with lasers or other techniques that are well known to those skilled in the art. The initial pattern cut into the tube includes sufficient spacing between link and ring components such that the stent can be crimped onto a catheter without causing general abutment of the ring and link components with each other. During deployment of the stent catheter through tortuous coronary arteries, the pattern also permits longitudinal movement of the link components without disturbing the crimp of the ring components. The need for spacing between the components in the crimped condition must be balanced with the need to provide improved scaffolding of the vessel being treated. That is, a relatively abundant number of links provides improved scaffolding of the vessel but potentially interferes with the ability to crimp the stent onto the catheter.

In another aspect of the invention, the stent configuration has undulating peaks and valleys of adjacent rings paired with each other in an in-phase relationship. Such a configuration can allow interconnecting links to nest within the peaks and valleys of the rings by providing at least two angled segments in a central portion of the link.

The compressed stent of the present invention can be securely mounted onto a very low profile, fixed wire catheter by incorporating relatively sharp angled bends instead of gentle curves and by placing adjacent portions of links and rings close together to provide the spacing needed for more compact nesting of the ring and link components. A further aid in reducing the minimal crimp diameter of the stent is to make the rings and links as narrow as possibly permitted by other design constraints. Thus, in the present invention, large numbers of connecting links can be included within a stent design having a very low minimal crimp diameter.

DESCRIPTION OF THE PREFERRED EMBODIMENT

Figure 1:
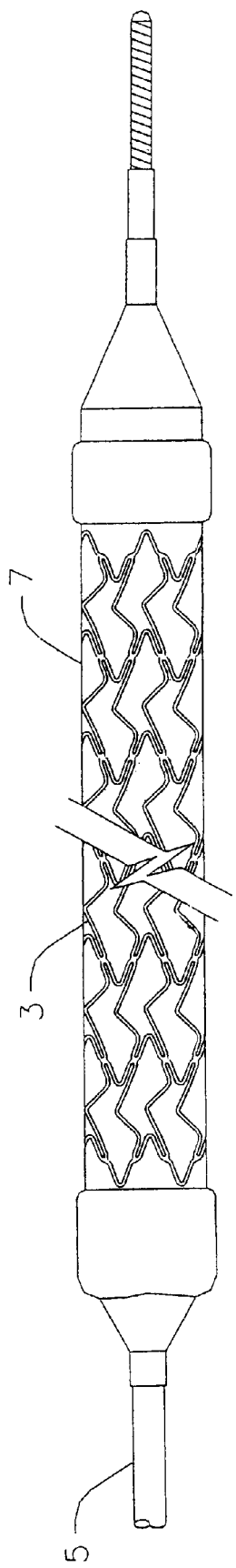
FIG. 1 is a side view of the stent of the present invention, shown mounted on a delivery catheter.
Figure 2:
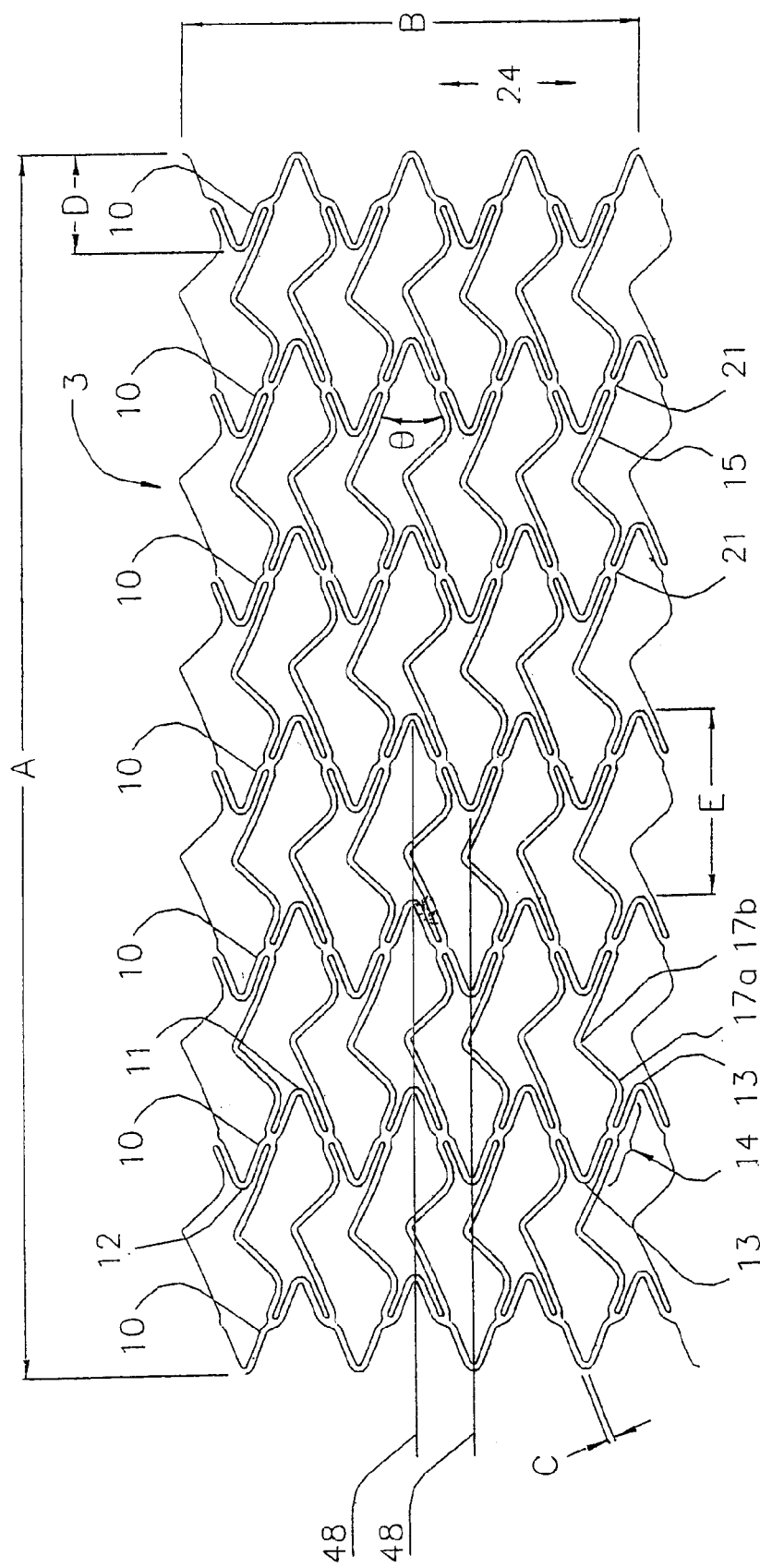
FIG. 2 is a plan view showing an opened and flattened stent made according to the present invention.

Stent 3 of the present invention, shown mounted on delivery catheter 5 in FIG. 1, has hollow, cylindrical body 7 made with a plurality of rings 10. Stent 3 can be made from a tube of stainless steel or other suitable material by laser cutting or other methods well known to those skilled in the art. As shown in FIG. 2, stent 3 has been cut open longitudinally and laid flat for convenience in description. Stent 3 is shown as it would appear after manufacture, in an uncrimped and unexpanded condition. Each of rings 10 extend circumferentially around cylindrical body 7 of stent 3 and include an undulating series of peaks 11 and valleys 12. Undulating peaks 11 and valleys 12 of rings 10 are formed by opposing angled segments 13, which are joined to each other by substantially straight struts 14. Adjacent rings 10 are joined together in a repeating pattern by a series of asymmetrical links 15, which are shaped and arranged to promote a very low crimp diameter, longitudinal flexibility during delivery, and effective scaffolding after deployment. Adjacent rings 10 are oriented such that undulating peaks 11 and valleys 12 are paired with each other in an in-phase relationship. FIG. 2 shows longitudinal axes 48, extending through adjacent peaks 11 and valleys 12 of rings 10. Link 15 is provided to interconnect rings 10 at inflection points 21.

Inflection points 21 are shown substantially centered on struts 14 between peaks 11 and valleys 12 of rings 10. At each inflection point 21, a portion of ring 10 extends in a generally circumferential direction (indicated with reference numeral 24) for a short distance, resulting in an offset in otherwise straight strut 14. The end portions of links 15 are arranged closely parallel to struts 14, and links 15 are joined to opposite sides of inflection points 21, forming a central orthogonal joint in strut 14. As an alternative description of the same structure, each strut 14 may be considered as including two parallel limbs extending from a central inflection point 21, and having the end of each limb connected to either link 15 or angled segment 13, which forms either peak 11 or valley 12. In strut 14, the parallel limbs that connect to links 15 are diagonally opposed to each other across the orthogonal joint, or inflection point 21. The limbs are narrow and formed closely parallel to each other to make the overall width of strut 14 as narrow as possible.

FIG. 2 depicts a cut open stent that has been manufactured according to the present invention and can it expand to become a nominal size of 2.5 mm in diameter and 15 mm in length. In this example, stent 3 was cut from metal tubing of about 1.7 mm in diameter. Preferably, as shown in this example, the tubing selected for making stent 3 has a diameter measuring about 70% of the nominal, expanded stent diameter. With this proportion between the diameters of expanded stent 3 and the tubing from which it is made, narrow struts 14 and sharply angled bends 13 combine to yield an angle θ between adjacent struts 14 that generally exceeds 40°. In the example shown in FIG. 2, angle θ measures 42°. By forming peaks 11 and valleys 12 with angled bends 13 instead of broader curves, struts 14 can be deformed closely parallel to each other when peaks 11 and valleys 12 are compressed. When stent 3 is compressed, the narrowness of struts 14 and their close, compressed arrangement provides a smaller crimped circumference (and diameter) than was achievable in previous stents.

Links 15 join inflection points 21 on adjacent rings 10. To promote the ability of stent 3 to flex longitudinally when it is subjected to bending forces, such as those encountered during delivery through a tortuous coronary artery, each link 15 includes at least two angled segments 1 7a–b. In the present invention, link 15 is made as short as possible to reduce the amount of material to be crimped into a small diameter without compromising flexibility and scaffolding properties. In order to reduce the length of links 15, segments 17a–b are formed with angles greater than about 90°, and segments 17a–b may be confined, generally, between adjacent longitudinal axes 48. Optionally, angled segment 17b extends across an axis 48, by approximately the width of link 15. Like angled segments 13, angled segments 17a–b are formed as tight angled bends, instead of broader curves, to promote compression of stent 3 to smaller diameters. Angled segment 17b of link 15 is located centrally between adjacent rings 10, and one end of link 15 includes angled segment 17a, while the other end extends in a substantially straight line from angled segment 17b to its connection at inflection point 21.

Connecting links 15 are positioned such that when stent 3 is expanded, links 15 will assist in providing scaffolding adjacent inflection points 21. Links 15 also extend past peaks 11 or valleys 12 to provide scaffolding in the space between adjacent rings 10. Circumferentially adjacent asymmetrical links 15 are longitudinally reversed with respect to each other. This means that if angled segment 17a is located to the right of angled segment 17b in first link 15, then, in links 15 located immediately above and below first link 15, angled segments 17a are located to the left of angled segments 17b. Angled segments 17a bend in the opposite direction from angled segments 17b, and both segments 17a–b preferably have the same angle. The above shapes and arrangement of rings 10 and links 15 provide relatively large "cell" size (i.e. the size of the smallest repeating unit in the pattern) to provide more space for elements to move into during compression of stent 3, thus permitting a very low crimped profile.

Stent 3 has a length "A" of about 8 to 30 mm for a coronary artery application. As illustrated in FIG. 2, length "A" could measure about 15–25 mm. Those skilled in the art will appreciate that the pattern of the invention can be configured to give many different lengths. Dimension "B" refers to the uncrimped, as-manufactured circumference of stent 3. For application in a coronary artery, which can be about 3–7 mm in diameter, the uncrimped diameter of stent 3 can measure about 1–2 mm. In the preferred embodiment, rings 10 and links 15 have the same width "C", which can be in the range of about 0.04 to 0.10 mm, and preferably measure about 0.065 mm. Dimension "D" refers to the amplitude of one of rings 10, which, in this example, could be in the range of about 0.75 to 2.5 mm. Dimension "E" refers to the peak-to-peak spacing for rings 10, which, in this example, could be in the range of about 1–3 mm. The preferred spacing between the parallel limbs of strut 14 is less than 0.10 mm, and more preferably, about 0.084 mm. Using the preferred dimensions given above with a preferred selection of four peaks 11 per ring 10, the 2.5 mm diameter stent in this example can achieve a minimal crimped diameter of about 0.74 mm (0.029 in.). This very low crimped profile is obtained by the present invention without compromising other important design features, such as longitudinal flexibility of the compressed stent, or the scaffolding strength of the final, expanded stent.

Those skilled in the art will further appreciate that the present invention may be embodied in other specific forms without departing from the spirit or central attributes thereof. In that the foregoing description of the present invention discloses only exemplary embodiments thereof, it is to be understood that other variations are recognized as being within the scope of the present invention. Accordingly, the present invention is not limited to the particular embodiments which have been described in detail herein.

I claim:

1. An endovascular stent comprising:

a hollow cylindrical body comprised of a first ring and a second ring, each of the rings having a width and extending circumferentially around the cylindrical body, each ring including an undulating series of peaks and valleys formed by opposing angled segments joined to each other by straight segments;

an inflection point interrupting at least one straight segment on each of the first and second rings to produce a generally circumferential offset in each of the segments;

a link joining the first and second rings by extending between the inflection point on the segment of the first ring and the inflection point on the segment of the second ring, the link having:

a width approximately equal to the width of the first and second rings;

a central angle;

a first substantially straight end; and a second end including an angle nearly equal to, and bending in the opposite direction from the central angle of the link, the first and second ends having substantially equal lengths and extending from the central angle of the link, wherein the link is asymmetrical about a radial plane located at the central angle.

2. The stent of claim 1 wherein each of the opposing angled segments of the rings has an included angle of at least about 40°.

3. The stent of claim 1 wherein the inflection point is substantially centered between a peak and a valley.

4. The stent of claim 1 wherein the first and second rings each include the same number of inflection points.

5. The stent of claim 1 wherein the first and second rings are joined by a plurality of the links.

6. The stent of claim 5 wherein circumferentially adjacent links are longitudinally reversed with respect to each other.

7. The stent of claim 1 wherein the peaks of the first ring are aligned on common longitudinal axes with the valleys of the second ring, and the valleys of the first ring are aligned on common longitudinal axes with the peaks of the second ring.

8. The stent of claim 7 wherein the link lies completely between adjacent longitudinal axes joining peaks and valleys.

9. The stent of claim 7 wherein the link extends beyond one of the adjacent longitudinal axes by no more than the width of the link.

10. An endovascular stent having a nominal expanded diameter and, as manufactured from a cylindrical tube, the stent comprises:

a first ring and a second ring, each of the rings extending circumferentially around the cylindrical tube in an undulating series of peaks and valleys formed by opposing angled segments joined to each other by straight struts, each strut having two ends, and each end having first and second parallel limbs extending from an orthogonal joint located centrally on the strut, the first limb at each end of the strut being joined to one of the opposing angled segments; and a link connecting the first and second rings by extending between one of the second limbs in the first ring and one of the second limbs in the second ring, the link having a first angle located centrally between the first and second rings, one end of the link being substantially straight and aligned with the second limb in the first ring, the other end of the link forming a second angle where it joins the second limb of the second ring, the second angle being about equal to the first angle, the second angle bending in the opposite direction from the first angle, the first and second ends of the link having substantially equal lengths and extending from the first angle of the link, wherein the link is asymmetrical about a radial plane located at the central angle.

11. The stent of claim 10 wherein the stent, as manufactured, has a diameter that is approximately 70% of the nominal expanded diameter of the stent, and each of the angled segments of the rings has an included angle of at least about 40°.

12. The stent of claim 10 wherein the first and second rings each include the same number of orthogonal joints.

13. The stent of claim 10 wherein the first and second rings are joined by a plurality of the links.

14. The stent of claim 13 wherein circumferentially adjacent asymmetrical links are longitudinally reversed with respect to each other.

15. The stent of claim 10 wherein each of the first limbs on each end of each strut are offset extensions of each other through the orthogonal joint of the strut.

16. The stent of claim 10 wherein the peaks of the first ring are aligned on common longitudinal axes with the valleys of the second ring, and the valleys of the first ring are aligned on common longitudinal axes with the peaks of the second ring.

17. The stent of claim 16 wherein the link lies completely between adjacent longitudinal axes joining peaks and valleys.

18. The stent of claim 16 wherein the link extends beyond either one of the adjacent longitudinal axes by no more than about the width of the link.

19. The stent of claim 10 wherein the angled segments, limbs and links all have the same width.

* * * * *